United States Patent [19]
Giri et al.

[11] Patent Number: 5,604,118
[45] Date of Patent: Feb. 18, 1997

[54] EUKARYOTIC EXPRESSION VECTOR SYSTEM

[75] Inventors: Chandrakant P. Giri, Rockville, Md.; Hiroyasu Ogawa, Osaka, Japan; Curtis C. Harris, Bethesda, Md.

[73] Assignee: The United States of America as represented by the Department of Health and Human Services, Washington, D.C.

[21] Appl. No.: 158,087

[22] Filed: Nov. 24, 1993

Related U.S. Application Data

[63] Continuation of Ser. No. 34,652, Mar. 22, 1993, abandoned, which is a continuation of Ser. No. 539,812, Jun. 18, 1990, abandoned.

[51] Int. Cl.⁶ ................................................. C12P 19/34
[52] U.S. Cl. ........................... 435/91.1; 435/6; 435/91.21; 435/91.4; 435/91.41; 435/91.5; 435/320.1; 435/172.3; 435/975; 536/23.1; 536/23.5; 536/24.1; 536/25.3; 935/2; 935/9; 935/22; 935/32; 935/80
[58] Field of Search .................. 435/6, 91.21, 91.4, 435/91.41, 91.5, 91.1, 320.1, 172.3, 975; 536/23.1, 23.5, 24.1, 25.3; 935/2, 9, 22, 32, 80

[56] References Cited

U.S. PATENT DOCUMENTS 5,238,834  8/1993  Pruitt ................................. 435/172.3

OTHER PUBLICATIONS

Promega Catalog (1988–1989) pp. 2–3 of section 9.
Maniatis et al. 1989 in *Molecular Cloning*. A Laboratory Manual, Second Edition, Cold Spring Harbor Laboratory, Cold Spring Harbor, NY. pp. 10.3 and 10.6.
Palazzolo et al. 1987, Gene. 52. 197–206.
Forster et al. 1985. Nuc. Acids Res. 13, 745–761.
Sambrook et al. (eds.) 1989 in: *Molecular Cloning*. A Laboratory Manual, Second edition. Cold Spring Harbor, New York, pp. 8.48–8.49, 10.40–10.43.
Asubel et al 1988. *Current Protocols in Molecular Biology*. vol. 2, John-Wiley & Sons., N.Y. pp. 12.6.1–12.6.9.
Okayama et al. 1987. Methods Enzymol. 154, 3–28.
Sargent 1987. Methods Enzymol. 152, 423–433.
*Pharmacia LKB Molecular Biology Products* 1988 Catalog.
*Pomega Biotec Biological Research Products* 1986/1987 Catalog.
Margolskee et al. 1988 Molec. Cell. Biol. 8, 2837–2847.
Duguid et al. 1988 Proc. Natl. Acad Sci. USA. 85, 5738–5742.

*Primary Examiner*—Christopher S. F. Low
*Attorney, Agent, or Firm*—Morgan & Finnegan L.L.P.

[57] ABSTRACT

The present invention relates to two plasmid vectors and eucaryotic expression vector created therefrom. The present invention further relates to a method of cloning a gene in a eucaryotic cell the expression of which is affected by drug treatment, a method of constructing a subtracted cDNA library and a method of identifying a eucaryotic gene the product of which inhibits cell growth.

2 Claims, 8 Drawing Sheets

EUKARYOTIC EXPRESSION VECTOR SYSTEM

This is a continuation of application Ser. No. 08/034,652, filed on Mar. 22, 1993 now abandoned, which is a continuation of Ser. No. 07/539,812, filed Jun. 18, 1990 now abandoned.

BACKGROUND OF THE INVENTION

1. Field of the Invention

The present invention relates to DNA constructs for and methods of cloning eucaryotic genes.

2. Background Information

To molecularly clone genes where hybridization or immunological probes are not available but where a given phenotype can be selected in eucaryotic cells, it is necessary for the construction of eucaryotic expression cDNA libraries containing a high proportion of full-length cDNAs. For the construction of libraries with a high proportion of full length cDNA of unknown genes vector-primed cDNA synthesis is employed.

In this context, a novel method based on vector-primed cDNA synthesis for high-efficiency cloning of functional cDNAs, which can be expressed in mammalian cells under the control of SV40 transcriptional elements, was developed by Okayama and Berg [Okayama and Berg, Mol. Cell. Biol., 3:280 (1983)]. Synthesis of a first strand of cDNA is primed by oligo (dT) covalently linked to a linear DNA which is derived from the plasmid vector, pcDV1, carrying SV40 polyadenylation signal. Monopolymeric dC tails are enzymatically added to the 3'-hydroxyl terminus of the newly synthesized cDNA. The dC tail added simultaneously to the 3'-terminus of the vector plasmid are removed by digestion with a restriction enzyme. The plasmid vector is then circularized with a linker DNA that carries a cohesive terminus at one end and a homopolymeric tail of dG residues at the other. The linker DNA, derived from the plasmid vector pL1, also carries nucleotide sequences for the SV40 "early" promoter. The dG residues pair with the dC tail of the first strand of cDNA and serve as primers for replacement synthesis of the second strand of cDNA catalyzed by RNase H and *E. coli* DNA polymerase I.

Recently, Margolskee et al. [Margolskee et al., Mol. Cell. Biol., 8:2837 (1988)], have developed a shuttle vector designated as EBO-pcD in which cDNA expression libraries constructed in the Okayama-Berg cDNA cloning vector system can not only be propagated and amplified in bacteria, but also can be stably replicated episomally in high copy numbers and expressed in human cells following cloning of EBO segment. The EBO segment of the plasmid DNA contains a resistant marker for hygromycin B (hph) to permit selection for stable transfectants of human cells, in addition to Epstein-Barr virus (EBV) origin of DNA replication and EBV nuclear antigen (EBNA) genes to ensure maintenance of stable and extrachromosomal replication of expression cDNA libraries in transformed human cells. Furthermore, since entire cDNA expression plasmid libraries can be maintained episomally and in high copy numbers in eucaryotic cells, intact cDNA clones can readily be "rescued" from individual transformants and recovered by propagation in bacteria. Hence, the ability to directly select for expression of cDNA clones corresponding to rare messages and, more significantly, to then recover these episomes for further functional characterization studies should make it possible to clone certain genes where hybridization and immunological screening methods are not available, but where a cellular phenotype can be selected in human cells.

Despite the recent advances such as the EBO system, it is still very difficult to clone rare cDNA clones in the Okayama-Berg vector primed cDNA synthesis system without concurrent cDNA subtraction. However, since it is not economically feasible to obtain enough poly(A)+ RNA from human cells in culture to perform subtraction, conventional methodology to subtract cDNA libraries based on cDNA:RNA hybridization is not possible in the human cell system.

SUMMARY OF THE INVENTION

It is an object of the present invention to provide a vector primed cDNA synthesis system wherein full length cDNAs of genes characterized by their resulting phenotype are enriched.

It is one object of the present invention to provide a vector system capable of synthesizing sense and antisense RNAs in vitro to generate RNA probes for RNA:RNA hybridization-based subtraction method.

Furthermore, it is an object of the present invention to provide an RNA:RNA hybridization-based subtraction method.

It is another object of the present invention to provide a means of constructing a phagemid-based cDNA subtraction library.

It is a further object of the present invention to provide a means of enriching expression cDNA libraries with respect to relevant genes based on a given mammalian cell phenotype.

Various other objects and advantages of the present invention will be apparent from the drawings and the following description of the invention.

The present invention relates to DNA constructs for cloning eucaryotic genes, specifically, rare genes, and to methods of using same.

Clones #6 and 16, which were randomly selected from BEAS2B-R1DNA library in pLHC2-cD vector system, have 1.0 and 1.5 kbp size cDNA inserts, respectively. These plasmid clones were used as templates in RNA synthesis reactions in vitro catalyzed by SP6 or T7 RNA polymerases following linearizations by Sal1 or Not1 digestions, respectively. The radiolabeled RNAs were analyzed by agarose gel electrophoresis after denaturation with glyoxal and dimethyl sulfoxide followed by autoradiography.

Figure 5:
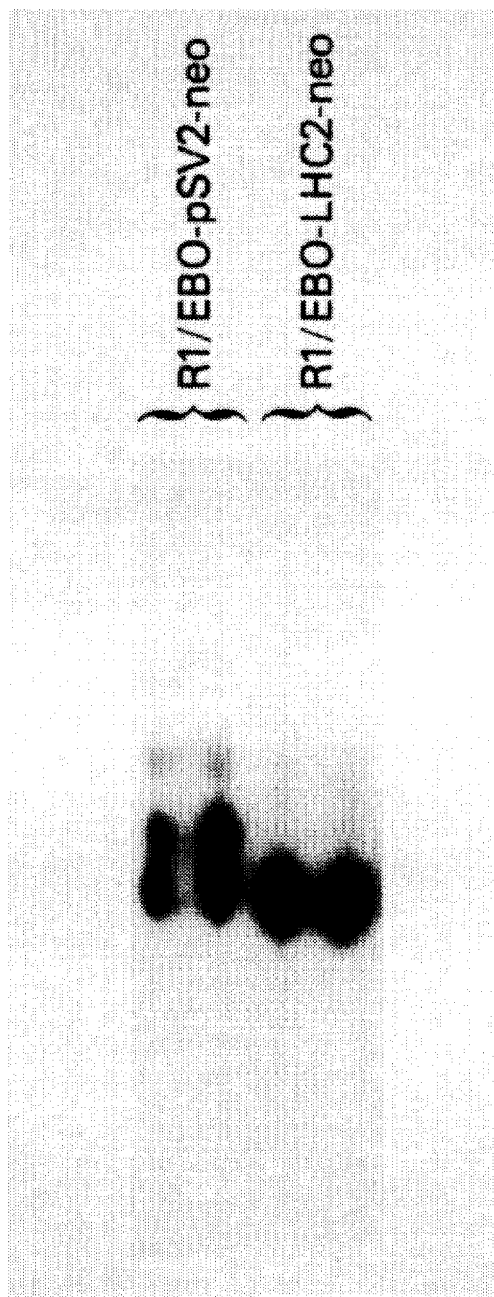

FIG. 5. Northern Blot Hybridization Analysis of Neo-specific RNAs expressed in vivo in hygromycin B as well as G418-resistant, stable transformants of BEAS2B-R1 Cells transfected with either EBO-pSV2-Neo or EBO-pLHC2-cD-Neo plasmids.

Human bronchial epithelial cell line, BEAS2B-R1, was transfected with either EBO-pSV2-Neo or EBO-pLHC2-cD-Neo plasmid DNA by the method of Brash et al. [Mol. Cell. Bio., 7:2031 (1987)]. Stable transformants were selected which were resistant to both hygromycin B and G418. Total RNAs (20 ug) isolated from these transformants were then electrophoresed in agarose gel containing formaldehyde. The RNAs were then transferred to nylon membrane filter, hybridized to radiolabeled Neo-specific probe, and then exposed at −70° C. for autoradiography.

Figure 6:
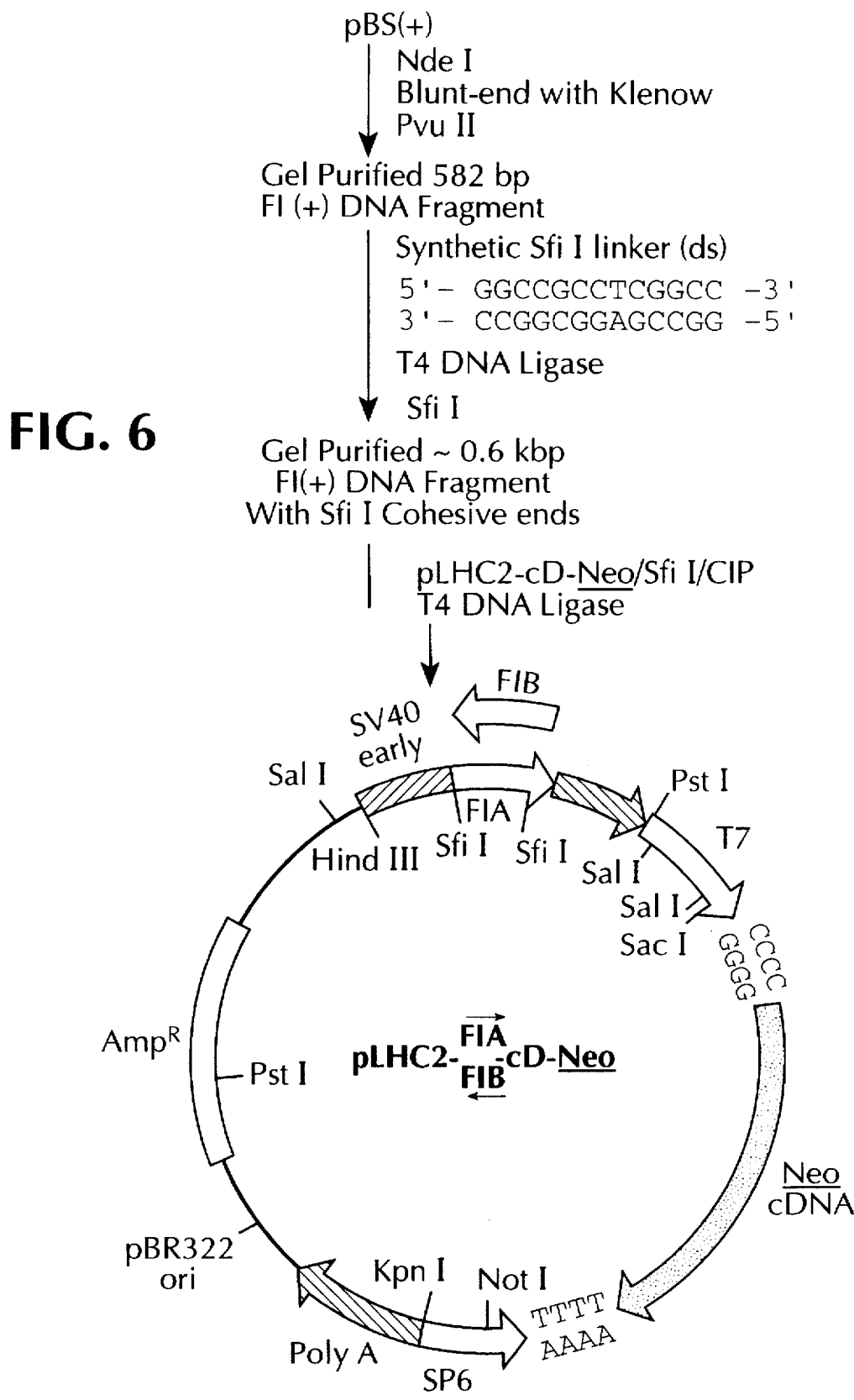

FIG. 6. Construction of pLHC2-(F1A DR F1B)-cD-Neo.

Figure 7:
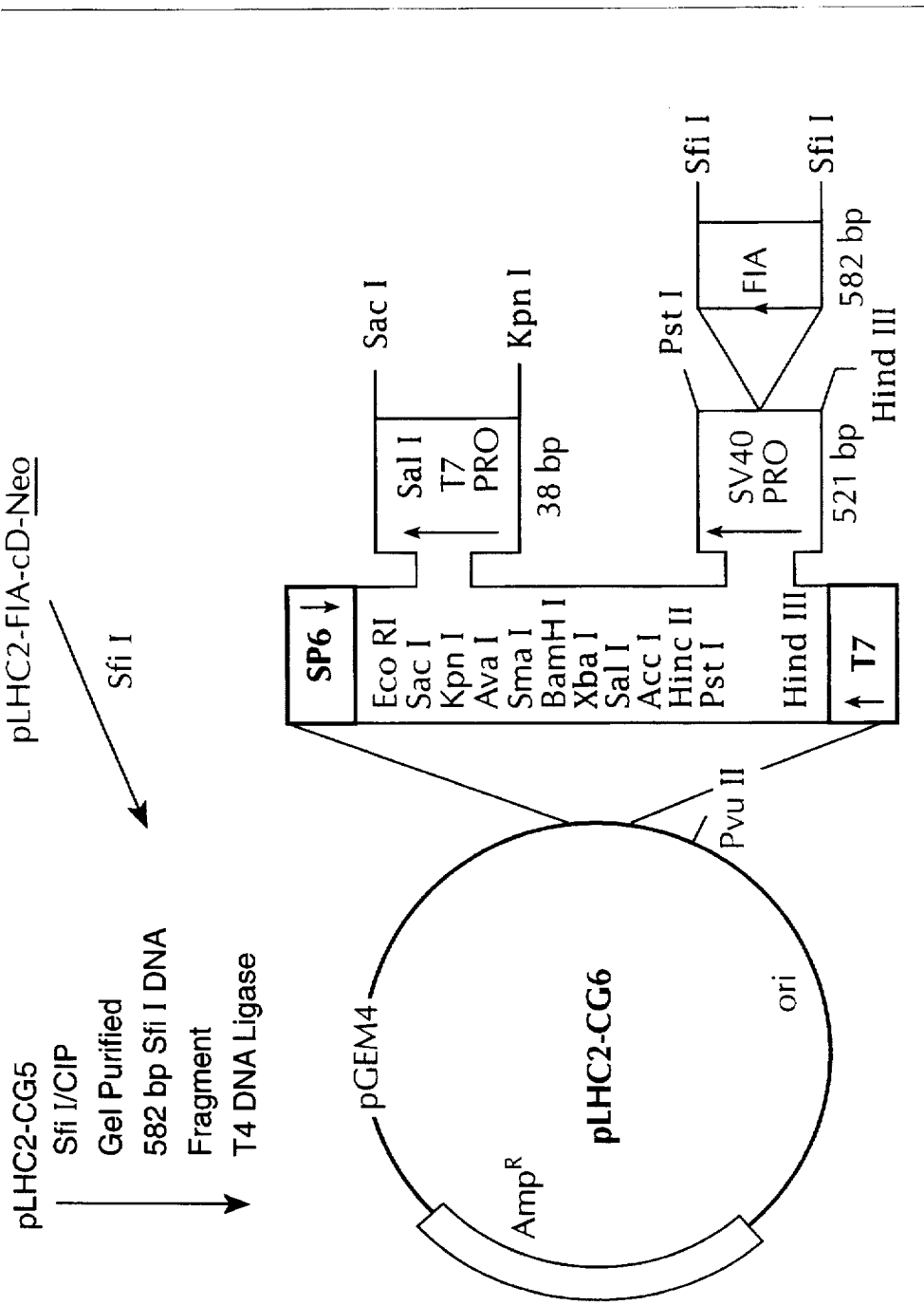

FIG. 7. Construction of pLHC2-CG6.

Figure 8:
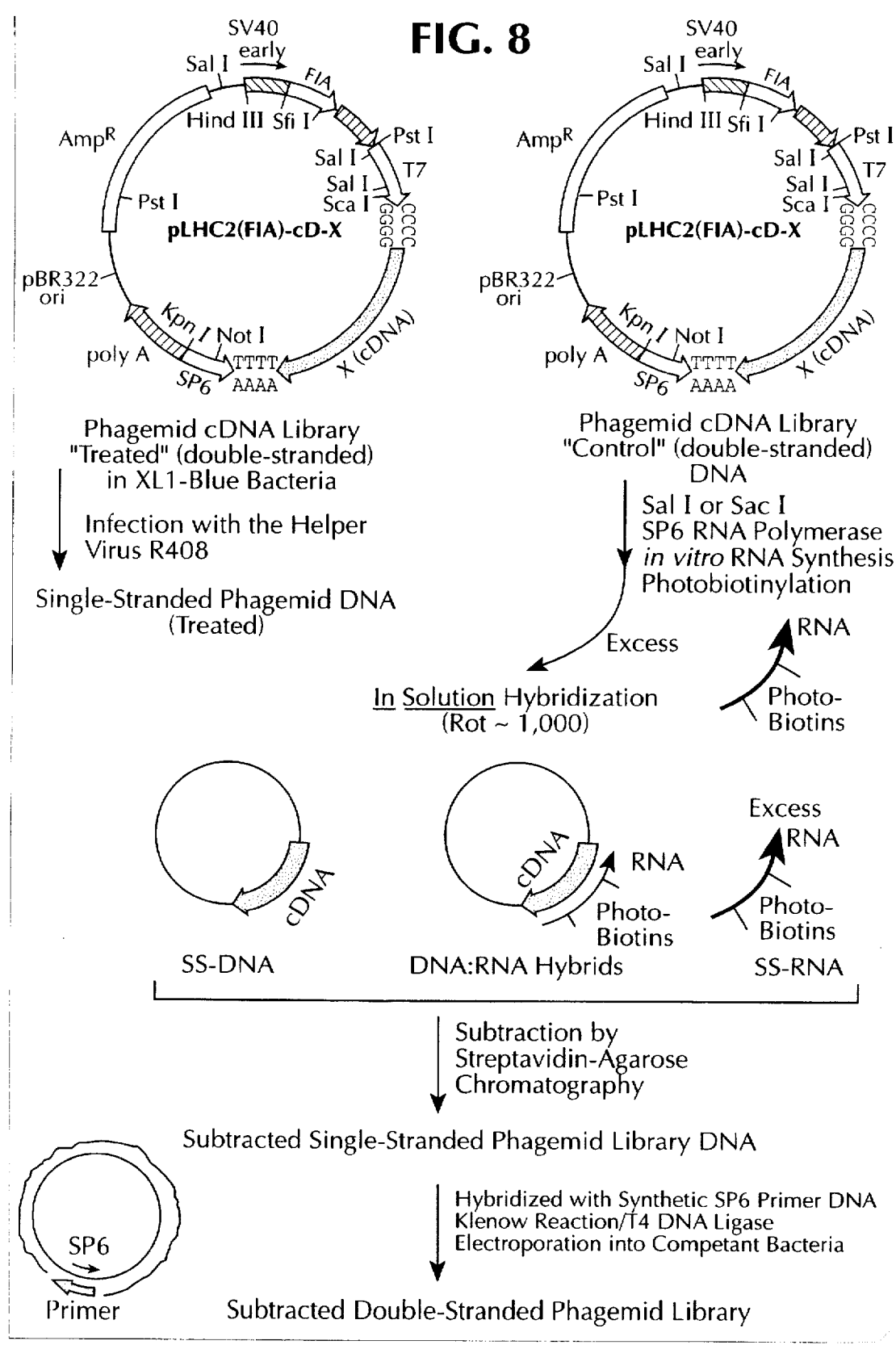

FIG. 8. Construction of Subtraction cDNA Libraries in pLHC2-cD-F1A Vector.

DETAILED DESCRIPTION OF THE PRESENT INVENTION

In one embodiment, the present invention relates to a eucaryotic expression vector, such as a mammalian expression vector, (see FIG. 3) comprising a eucaryotic promoter, such as, for example, an SV40 promoter, in clockwise orientation; a first bacteriophage polymerase promoter which is in clockwise orientation and downstream of the eucaryotic promoter; a DNA sequence encoding a eucaryotic protein, which is in clockwise orientation; a second bacteriophage polymerase promoter which is in counterclockwise orientation; and a polyadenylation signal in clockwise orientation operably linked to the second bacteriophage polymerase promoter and dA-dT sequence. The first bacteriophage polymerase promoter and the DNA sequence are operably linked via a deoxycytidilate-deoxyguanidylate (dC-dG) sequence of about 10 to 15 base pairs. The second bacteriophage polymerase promoter and the DNA sequence are operably linked via a deoxyadenylate-deoxythymidylate (dA-dT) sequence of about 40 to 60 base pairs, preferably about 45 to 50 base pairs. The RNA transcripts initiated from the first bacteriophage polymerase promoter are sense transcripts, whereas the second bacteriophage polymerase promoter initiates antisense RNA transcripts. Furthermore, the expression vector contains at least two differing rare restriction site, that is, restriction sites comprising at least 6 base pairs for linearizing the plasmid. Alternatively, instead of a rare restriction site a nucleotide sequence encoding a transcription termination site specific for a polymerase can be cloned into the vector. The first restriction site is located between the first bacteriophage polymerase promoter and the dC-dG sequence and correspondingly, the second restriction site is located between the second bacteriophage polymerase promoter and the dA-dT sequence.

As one skilled in the art will appreciate inherent in a eucaryotic expression vector is an origin of replication, preferably pBR322 origin of replication, and a selection marker, such as, for example, an ampicillin resistance gene. Accordingly, the expression vector of the present invention includes these elements.

Suitable bacteriophage polymerase promoters for use in the present expression vector include, but are not limited to, T3 and T7, preferably, SP6 and T7 promoters. In addition, possible rare restriction sites are, for example, NotI, SacI or SalI.

The above-described expression vector is constructed from two plasmid vectors due to vector-primed cDNA synthesis using methods previously described [Okayama and Berg, Mol. Cell. Biol., 3:280 (1983)]. The first plasmid vector (see FIG. 1) comprises a polyadenylation signal; a bacteriophage polymerase promoter, such as, for example, an SP6 promoter; at least one rare restriction enzyme sites each comprising at least 6 base pairs; and a restriction site unique to the plasmid that leaves, on digestion, a 3' protruding end, such as, for example, SacI. Within the plasmid vector the polyadenylation signal is oriented clockwise and conversely, the bacteriophage polymerase promoter is oriented counterclockwise. In addition, the unique restriction site is located downstream of the rare restriction site. Further, the bacteriophage polymerase promoter is located between the polyadenylation signal and the restriction enzyme sites which are downstream of the promoter. The polyadenylation signal, promoter and restriction enzyme sites are substantially adjacent to each other such that when the expression vector is constructed, the cDNA sequence, the dA-dT sequence and the polyadenylation signal are operably linked.

The second plasmid vector (see FIG. 2) comprises a eucaryotic promoter; a bacteriophage polymerase promoter, such as a T7 promoter; a rare restriction site comprising at least 6 base pairs; and a restriction site unique to the plasmid that leaves, on digestion, a 3' protruding end. The eucaryotic promoter and the bacteriophage polymerase promoter are in the same orientation within the plasmid vector and the bacteriophage polymerase promoter is downstream of the eucaryotic promoter. Further, the rare restriction site is downstream of the bacteriophage polymerase promoter and the unique restriction site is downstream of the rare restriction site.

Suitable eucaryotic promoters for use in the present invention include, but are not limmited to, SV40, stronger constitutive eucaryuotic promoters, such as, retroviral long terminal repeat (LTR) or cytomegalovirus (CMV), inducible promoters, such as, metallothionine or heat shock promoters.

The eucaryotic expression vector and correspondingly, the second plasmid vector of the present invention may further comprise a phage replication origin that packages single stranded DNA, such as, for example, a F1A origin of DNA replication (see FIG. 7). When the expression vector (or the second plasmid vector) contains the phage replication origin, the origin is located within the eucaryotic promoter in the same orientation or the opposite orientation as the eucaryotic promoter. The F1 bacteriophage origin of DNA replication within the vector system of the present invention allows the construction of phagemid-based cDNA subtraction libraries while retaining the advantages of vector-primed cDNA synthesis which is not currently possible with the Okayama and Berg vector system.

Alternatively, if the eucaryotic expression vector of the present invention does not include the phage replication origin, the eucaryotic expression vector may further comprise a sequence providing for episomal replication in eucaryotic cells, such as, for example, the sequence may comprise a Epstein-Barr virus origin of replication and Epstein-Barr virus nuclear antigen genes and a eucaryotic selection marker gene, such as, for example, hygromycin B (see FIG. 3), or histinol dehydrogenase. The sequence for episomal replication together with the marker gene is put in the eucaryotic promoter.

In another embodiment, the present invention further relates to a method of cloning a gene in a eucaryotic cell, such as, for example, a mammalian cell, the expression of which is affected by drug treatment. In this method, a eucaryotic cell population is divided into two aliquots. The first aliquot of cells is treated with an agent, such as a drug, inducing the expression of rare genes, that is, genes whose mRNA comprises 0.01 to 0.001% of the total mRNA of the cell prior to the drug treatment. A first cDNA library is constructed using the plasmid vectors of the present invention so that the cDNA corresponding to the messenger RNA of the first aliquot of drug treated cells is cloned in the eucaryotic expression vector of the present invention. A second cDNA library is also constructed, as the first library, in the expression vector of the present invention from messenger RNA of a second untreated aliquot of cells.

After the libraries are constructed, the first library is linearized with a rare restriction enzyme which cuts the expression vector at one of the bacteriophage polymerase promoter sites and is then treated in vitro with a polymerase, such as, for example, SP6 RNA polymerase or T7 RNA polymerase, specific for the other bacteriophage polymerase promoter present in the expression vector, in the presence of a radiolabeled nucleotide to generate a first group of RNA.

Figure 3:
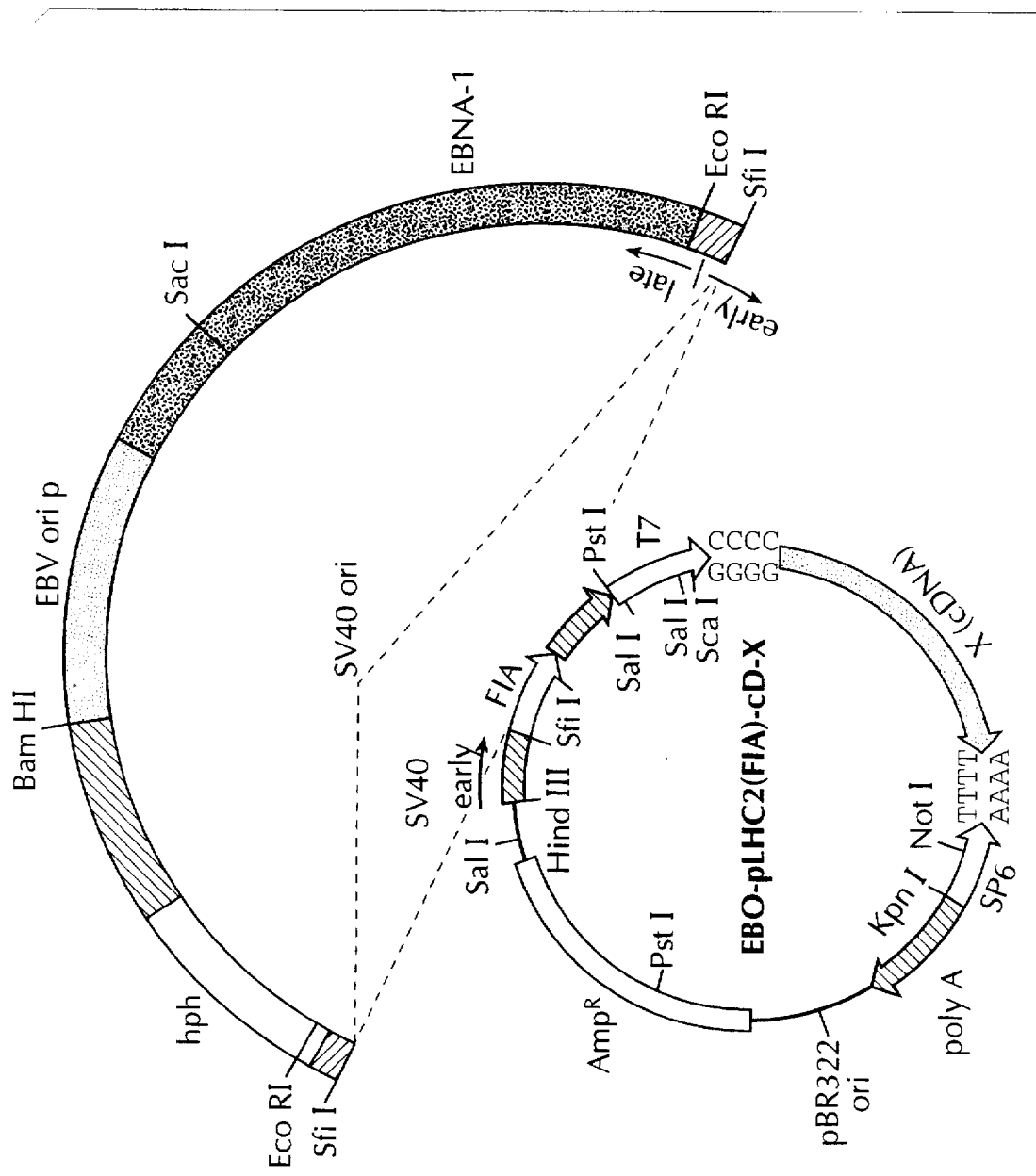
FIG. 3. EBO-pLHC2(F1A)-cD-X Phagemid Vector Map.

In addition, the second library is linearized with a rare restriction enzyme which cuts the expression vector at the bacteriophage polymerase promoter site remaining intact in the first library and in then treated in vitro with a polymerase specific for the other bacteriophage polymerase promoter to generate a second group RNA. That is, if in the first library, the expression vector shown in FIG. 3 is cut at the T7 promoter and the library is treated with SP6 RNA polymerase, then the second library is cut at the SP6 promoter and is treated with T7 RNA polymerase.

Prior to the subtraction step, the second group of RNA is photobiotinylated. Then the first group of RNA is contacted with the second group of RNA under conditions such that complementary RNA sequences can base pair to form double strand RNA:RNA hybrids. This is referred to RNA:RNA hybridization based subtraction. The double-stranded hybrids are separated out, preferably by streptavidin-agarose chromatography, thereby yielding subtracted radiolabeled single stranded RNAs which can act as subtracted probes for eucaryotic genes. These probes are used to screen the first library for cloned genes, the expression of which is affected by drug treatment.

One skilled in the art will appreciate that either the sense RNA or the antisense RNA can be generated from the first library depending on the selected restriction enzyme and RNA polymerase combination so long as the opposite is generated from the second library so that RNA:RNA hybridization can be effected.

Genes that are induced or repressed by the agent can be cloned using the above described method. When inducible genes are to be cloned, then as stated above, the RNA from the control cell is subtracted out of the RNA from the treated cell. If, on the other hand, repressed genes are to be cloned, the RNAs from treated cells are subtracted out of the RNAs from the control cells.

The RNA:RNA hybridization-based subtraction produces single stranded subtracted radiolabeled RNA probes to screen cDNA libraries. However, since the RNA probe is limited in quantity and half-life, it can only be used a finite number of times to screen libraries. Thus, even more desirable, is a subtracted cDNA library which can be repeatedly utilized in further studies.

Accordingly, in another embodiment, the present invention relates to a method of constructing a subtracted cDNA library (see FIG. 8) which comprises cDNA of eucaryotic genes to be identified and characterized by their phenotype, preferably genes which are naturally expressed in low copy numbers. As in the above-described cloning method, a population of cells are divided in two aliquots, one aliquot of which is then treated with an agent that induces the expression of rare genes. cDNA libraries are then constructed from the mRNA of the two aliquots as described in the above method utilizing the plasmid vectors and the expression vector of the present invention. It is necessary that the second plasmid vector used in this method includes the phage replication origin sequence in the same orientation as the eucaryotic promoter and the bacteriophage promoter so that the final expression vector will contain the phage replication sequence (for example, the plasmid vector pLHC2-CG6, shown in FIG. 7).

After construction of the libraries, a single-stranded DNA is generated from the first library by use of the phagemid replication origin using methods well known in the art.

The second library is linearized with a restriction enzyme cutting at the rare restriction site near the first bacteriophage polymerase promoter, for example SacI or SalI, and is treated in vitro with a polymerase, for example SP6 RNA polymerase, specific for the second bacteriophage polymerase promoter of the expression vector which transcribes in the opposite orientation as the phagemid replication origin. The resulting RNA is photobiotinylated and contacted with the single-stranded DNA produced from the first library under conditions such that complementary DNA and RNA sequences can base pair and form double-stranded DNA:RNA hybrids. The unhybridized DNA (subtracted single-stranded DNA) is separated from the double-stranded hybrids, such as, for example, by streptavidin-agarose chromatography.

The subtracted single-stranded DNA is treated with Klenow fragment of $E.\ coli$ DNA polymerase I and an oligodeoxynucleotide primer of about 20 to 30 nucleotides complementary to a segment of the expression vector encoded in the single stranded DNA, such as, to the SP6 promoter, under conditions such that double-stranded DNA is created. The double-stranded DNA may then be used to transform a suitable host bacteria to create a subtracted cDNA library.

Once the subtraction is accomplished, the F1 DNA sequence in the expression vector of the cDNA library can be substituted with the EBO DNA segment at a restriction site, such as, for example, SfiI. The EBO-subtracted cDNA library can then be used to transfect mammalian cells to screen for specific cDNA clones based on a given phenotype according to the EBO strategy of Margolskee et al. [Mol. Cell. Biol., 8:2837 (1988)] as described herein.

When, as described above, the phage replication sequence is in the same orientation as the eucaryotic promoter and bacteriophage polymerase promoter, then the second cDNA library is linearized at the restriction site near the first bacteriophage polymerase promoter and is treated in vitro with a polymerase specific for the second bacteriophage polymerase promoter. If, however, the phage replication sequence is in the opposite orientation as the eucaryotic promoter and bacteriophage polymerase promoter, then the second library is linearized at the restriction site near the second bacteriophage polymerase promoter and is treated with a polymerase specific for the first bacteriophage polymerase promoter. As one skilled in the art will understand, this is necessary so that both the sense and the antisense messages are encoded in the single stranded cDNAs and the single stranded RNAs.

As RNA:RNA and RNA:DNA hybrids are more stable than DNA:DNA hybrids, the present methods are advantageous since hybridization can be preformed under higher stringency conditions and can be achieved with less degradation complications. The use of high stringency conditions is especially important in the isolation of rare messages since a double stranded mismatch pairing could easily remove the limited copies of the desired message. Furthermore, the use of streptavidin-agarose (SA) chromatography is an improvement in the separation of double stranded complexes, such as RNA:RNA hybrids, from single stranded sequences, such as RNA. Separation of single and double stranded nucleic acids by SA chromatography is much simpler and efficient than separation by conventional hydroxylapatite chromatography. Two cycles of in solution hybridization, for example, RNA:RNA or RNA:DNA, followed by SA chromatography, on average, 98% subtraction can be achieved.

Use of the Klenow fragment of E. coli DNA polymerase for the conversion of single stranded phagemid DNA to double stranded DNA is another major improvement. The present inventors have found the Klenow fragment to be about 270-fold more efficient than the conventional use of reverse transcriptase.

In a further embodiment, the present invention relates to a method of identifying a eucaryotic gene, the product of which inhibits cell growth. The present method is especially useful in identifying genes involved in the regulation of growth inhibition, terminal differentiation, tumor suppression and senescence.

In the present method a subtraction cDNA library is created from cells treated with a agent inducing the expression of growth inhibitory genes as in the above described method. Once double stranded DNA encoding the growth inhibitory genes have been created, a sequence providing for episomal replication in eucaryotic cells substituted in place of the phage replication sequence via a restriction site. Next, growth inhibited eucaryotic cells are generated by treatment with the agent previously used on the first aliquot of cells. These growth inhibited cells are transfected with (i) the double stranded DNA and (ii) a eucaryotic expression vector. This vector comprising a bacteriophage polymerase gene whose product is specific for the promoter of the eucaryotic expression vector which generates antisense RNA in mammalian cells, a nuclear targeting sequence, and a selection marker differing from the selection marker of the eucaryotic expression vector. The cells can be pre-transfected or co-transfected with the double stranded DNA and the vector using methods well known in the art. Cells which resume growth should be highly enriched in the inhibitory genes of interest which have been turned off due to the expression of antisense RNA within the cell. The cDNA encoding the gene is obtained by isolating the episomally replicating plasmid from the growing cells.

As one skilled in the art will appreciate, when a gene induced by the treatment is desired, then as described above, the single stranded DNA is generated from the treated aliquot. Whereas, if the desired gene is repressed by the treatment, the single stranded DNA is generated from the control, untreated aliquot and the treated aliquot is subtracted therefrom.

EXAMPLES

Materials

Okayama-Berg plasmid vectors, pcDV-1 and pL1, were purchased from Pharmacia, whereas pBS(+) was procured from Stratagene. Neo RNA was obtained from the cDNA synthesis kit sold by Behringer-Meinheim. Synthetic oligodeoxynucleotide linkers bearing SP6 or T7 promoter DNA sequences along with specific restriction enzyme sites were custom synthesized, purified, and phosphorylated by the Midland Certified Reagent Company. Other synthetic DNA linkers were synthesized on a DNA Synthesizer, Model 381A, manufactured by the Applied Biosystems. Restriction enzymes, polynucleotide kinase, T4 DNA ligase, Klenow fragment of DNA polymerase I, terminal deoxynucleotide transferase (TdT), RNaseH, etc. were purchased from Pharmacia, New England BioLabs, or Bethesda Research Laboratory. Reverse transcriptase was procured from Seikagaku Company. In vitro synthesis of RNA was performed using the kit purchased from Promega Corporation. The helper phage R408 was from Invitrogen Company. The bacterial strains, SCS-1 and XL1Blue were from Stratagene and WM1100 was obtained from BioRad Company. Unless specified otherwise, all recombinant DNA methods were adapted from Maniatis [Maniatis, T., (1982). Molecular Cloning: A laboratory manual. Cold Spring Harbor Laboratory Press].

Construction of Expression cDNA Libraries in the pLHC2-cD Vector System

Construction of the pLHC2-cD vector system was based on modification of the vector-primed cDNA synthesis protocol of Okayama and Berg [Okayama and Berg, Mol. Cell. Biol., 3:280 (1983); Okayama et al., Methods in Enzymology, 154:3 (1987)]. Briefly described as follows.

For extraction and purification of poly(A)+ RNA from human cells, total RNA was extracted from monolayer cultures of human cells with 6M guanidinium thiocyanate followed by centrifugation in cesium chloride solutions [Chirgwin et al., Biochemistry, 18:5294 (1979)]. Poly(A)+ RNA was purified from the total RNA preparation by at least two cycles of oligo-dT cellulose chromatography. Intactness of the poly(A)+ RNA preparations were tested by northern blot hybridization analyses of GAPDH message. Functional analyses were performed by template activity (ug cDNA synthesized per ug RNA template used times 100) determination using oligo-dT as well as dT-tailed pLHC2-cD vector as primers. Using oligo-dT as primer and AMV reverse transcriptase (RT) from Seikagaku Company, template activities of the poly(A)+ RNA preparations were in excess of 30%.

For first-strand cDNA synthesis catalyzed by AMV-RT, the optimal ratio of dT-tailed vector-primer to poly(A)+ RNAs was about 2 ug:5 ug, respectively.

For dG-tailing of cDNAs, an inclusion of poly(rA) in the reaction mixture at a concentration of 0.015 ug/ul was found to minimize preferential tailing of unutilized vector molecules as well as of cDNAs not covalently linked to the vector. This minimizes the number of cDNA clones with no inserts. The optimal tail-length was about 10–15 dG residues.

For HindIII digestion, the optimal conditions were found to be about 40 units of the freshly acquired enzyme and the digestion period was about 14 hrs.

For the cyclization mediated by oligo dC-tailed linker DNA and replacement of the RNA strand by DNA, the optimal molar ratio of vector to linker DNA was about 1:2, respectively.

For transformation of competent host bacteria, the efficiency of transformation using chemically-competent SCS-1 strain of bacteria was around $10^8$ transformants per ug pUC18 DNA. Using electroporation method of transformation of the bacterial strain WM1100, the present inventors were able to obtain up to $10^{10}$ transformants per ug pUC18 DNA (BioRad Gene Pulser and Pulse Controller). High quality deionized dH20 (Millex or HPLC Grade) must be used while preparing electrocompetent bacteria.

Photobiotinylation of RNAs was accomplished by labeling of RNAs with photobiotin acetate using the Subtractor Kit of the Invitrogen Company essentially as described by the manufacturer.

For streptavidin-agarose (SA) column chromatography, Poly-Prep chromatography columns (BioRad Company) were siliconized, DEPC-treated, autoclaved, and then packed with about 0.4 ml of streptavidin-agarose (Bethesda Research Laboratories). The column was equilibrated with about 5 column volumes of loading buffer (10 mM Tris-HCl, pH7.5—0.3M NaCl—5 mM NaEDTA—100 ug/ml of yeast tRNA—20 ug/ml of poly(rA). A 0.2 ml of the loading buffer containing sample photobiotinylated RNA along with 200 ug yeast tRNA and 20 ug poly(rA) as carriers was applied to the column and the flow-through was repeatedly (x4) reapplied to the column to ensure quantitative binding of the photobiotinylated RNA to the streptavidin-agarose column. The column was then washed with the loading buffer to quantitatively collect the unbound nucleic acids which are essentially non-photobiotinylated.

The original Okayama-Berg plasmid vectors, pcDV1 and pL1, have been modified to generate vector-primer and linker DNAs, respectively, as follows. To allow for synthesis of sense and antisense RNA transcripts from the cDNA inserts in vitro and in sufficient quantities to perform subtraction based on RNA:RNA hybridization, bacteriophage RNA polymerase promoter DNA sequences, SP6 and T7, in opposite transcriptional orientations along with rare restriction enzyme sites, Not1 and Sal1, have been cloned within the modified vector-primer and linker plasmids, designated as pLHC2-HO2 and pLHC2-CG5, respectively.

Figure 1:
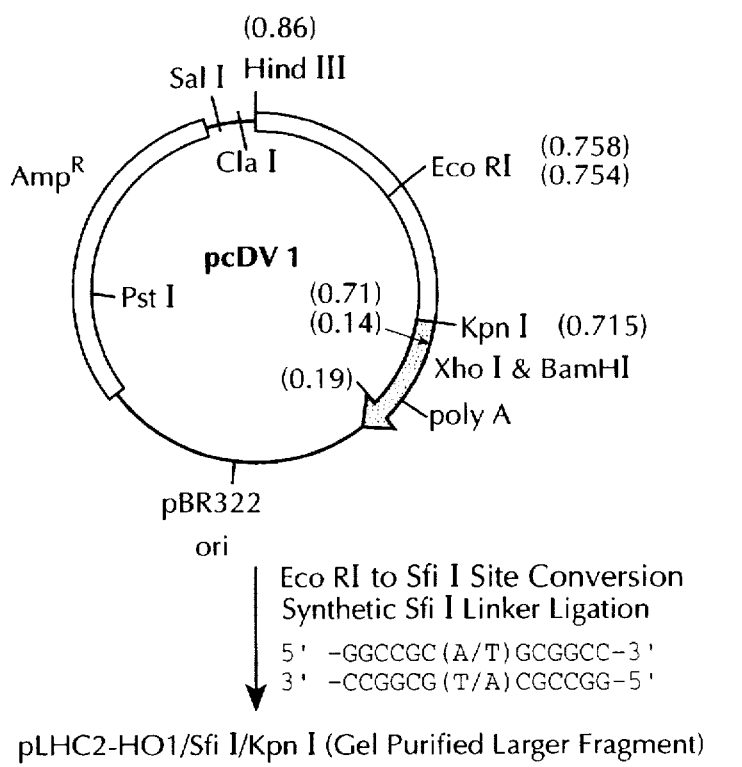
FIG. 1. Construction of pLHC2-HO2.
Figure 1:
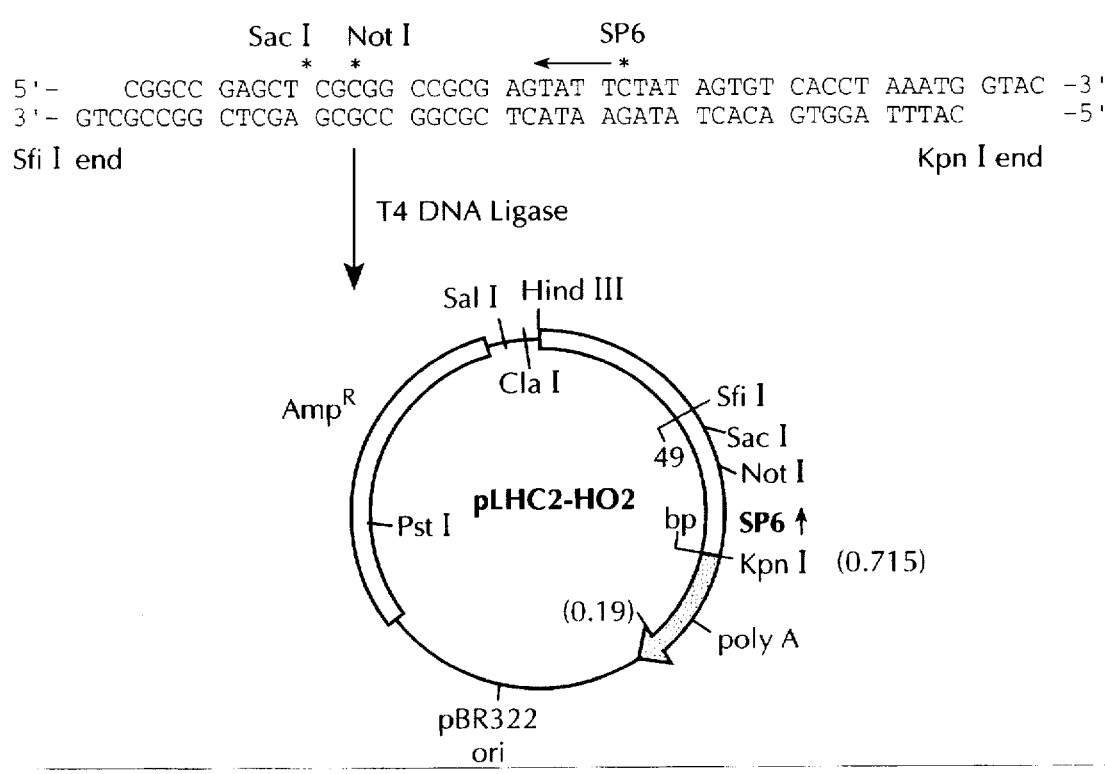

As shown schematically in FIG. 1, in the original Okayama-Berg vector-primer plasmid, pcDV1, the EcoR1 restriction site was converted to Sfi1 by synthetic Sfi1 linker ligation to generate the plasmid, designated as pLHC2-HO1. The pLHC2-HO1 plasmid was digested with Sfi1 and Kpn1 and the larger DNA fragment was gel-purified. A 49 bp synthetic double-stranded DNA containing Sac1 and Not1 restriction sites along with SP6 promoter sequence flanked by Sfi1 and Kpn1 cohesive ends was then ligated to pLHC2-HO1/Sfi1/Kpn1 to yield pLHC2-HO2.

A dT-tailed pLHC2-HO2 vector-primer was then prepared essentially according to Okayama and Berg [Mol. Cell. Biol., 3:280 (1983)]. Briefly, following Sac1 digestion of pLHC2-HO2, an average of 45 dT residues were covalently linked to the 3'-ends in a terminal deoxynucleotide transferase (TdT)-catalyzed reaction. The unwanted tail was removed by Sfi1 digestion. The resulting large DNA fragment was selectively precipitated with PEG-6000 and subsequently purified by oligo-dA cellulose column chromatography. This was then used as a dT-tailed vector-primer for reverse transcriptase-catalyzed cDNA synthesis.

Figure 2:
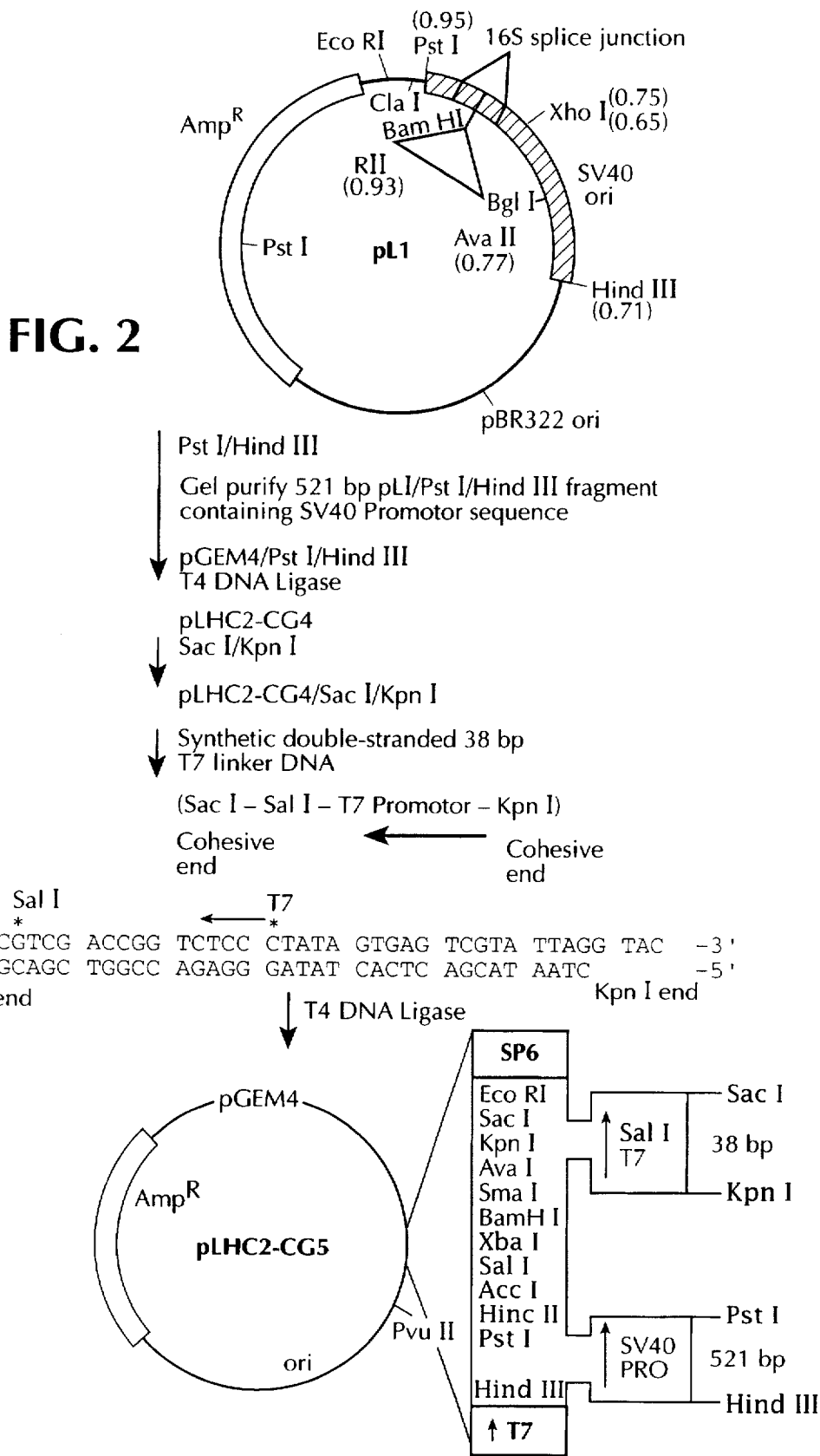
FIG. 2. Construction of pLHC2-CG5.

For construction of dC-tailed linker DNA plasmid, pLHC2-CG5, initially, the 521 bp linker DNA fragment from the original Okayama-Berg plasmid, pL1, was cloned into Pst1 and Hind3-digested pGEM4 cloning vector to use Sac1 and Kpn1 restriction sites in this vector. The resultant plasmid clone, designated as pLHC2-CG4, was digested with Sac1 and Kpn1. As shown in FIG. 2, a 38 bp synthetic double-stranded DNA with Sal1 restriction site and T7 promoter sequence flanked by Sac1 and Kpn1 cohesive ends was ligated into Sac1 and Kpn1-digested pLHC2-CG4 vector to generate pLHC2-CG5 which is the source plasmid for the preparation of linker DNA fragment according to Okayama and Berg [Mol. Cell. Biol., 3:280 (1983)], but modified as follows.

Briefly, pLHC2-CG5 was linearized by Sac1 digestion, and an average of 9 dC tails (instead of dG tails as in the Okayama and Berg protocol) were added to the 3'-ends of the linear DNA with Tdt. After Hind3 digestion, the 586 bp dC-tailed DNA fragment that contains SV40 and T7 promoter sequences was purified by agarose gel electrophoresis.

A cDNA insert, when cloned into the pLHC2-cD mammalian expression vector system according to Okayama-Berg protocol of vector-primed cDNA synthesis, would now be flanked by SP6 and T7 promoter sequences in opposite transcriptional orientations as shown schematically in FIG. 3. These procaryotic promoter DNA sequences allows for in vitro synthesis of sense and antisense RNAs to perform subtraction.

Using optimal conditions at each of the steps involved in the cDNA cloning scheme [Okayama et al., Methods in Enzymology, 154:3 (1987)], as described hereinabove, cDNA libraries from poly(A)+ RNA preparations isolated from human bronchial epithelial cell lines (BEAS2B-S6 and -R1) have been constructed. After correction for an estimated background of about 20–30% (i.e., cDNA insert size less than 0.2 kbp), the cDNA libraries constituted about $10^6$ independent cDNA clones per ug poly[A]$^+$ RNA.

The following functional analyses of various regulatory genetic elements within the cDNA cloning vector, pLHC2-cD were conducted.

Figure 4:
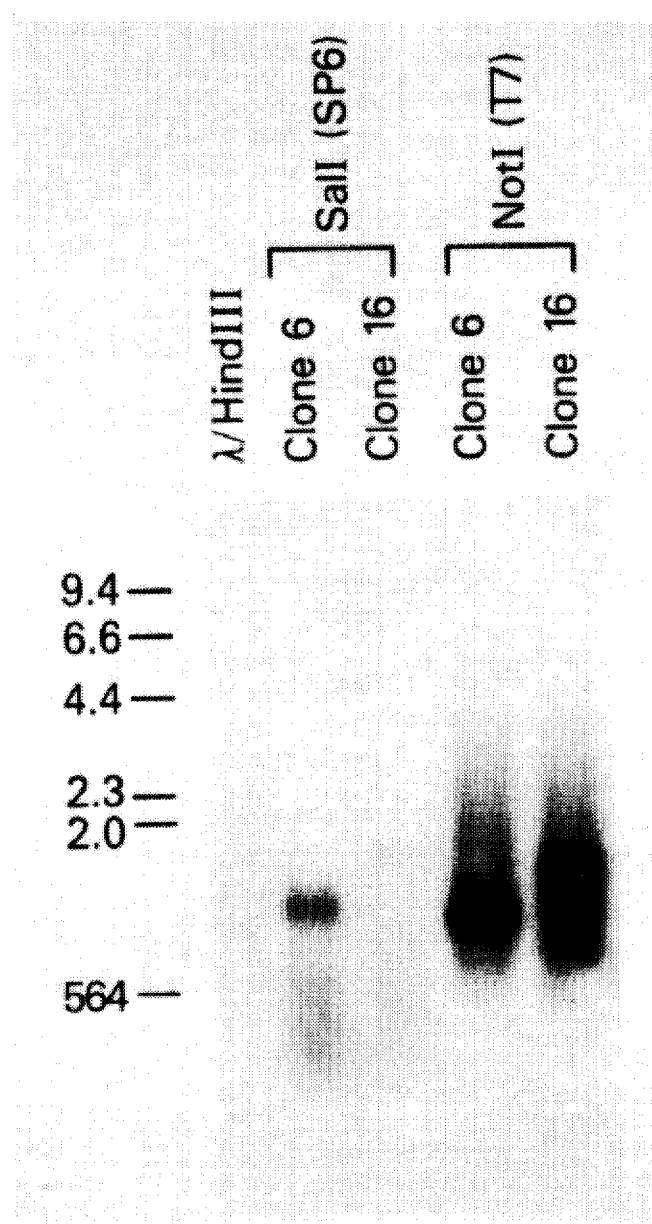
FIG. 4. In Vitro RNA Synthesis from BEAS2B-R1 cDNA Library Clones in pLHC2-cD Vector System.

In Vitro Analyses: The SP6 and T7 promoter DNA sequences along with Not1 and Sal1 restriction sites cloned into appropriate sites within the pLHC2-cD vector were tested to be functional based on the ability to synthesize RNA transcripts in vitro catalyzed by SP6 and T7 RNA polymerases, respectively, from randomly selected BEAS2B-R1 cDNA clones of about 1.0 to 1.5 kbp size range (FIG. 4).

In Vivo Analyses: To ensure that the SP6 and T7 promoter DNA sequences cloned strategically within the pLHC2-cD vector (see FIG. 3) did not adversely affect the expression of cDNA inserts under the transcriptional control of SV40 genetic elements, a mini-cDNA library consisting of partial to full-length clones was constructed from commercially available (Behringer-Meinheim) 1.1 kb poly(A)+ RNA encoding for neo-resistant gene, essentially as described above for BEAS2B cDNA libraries in the pLHC2-cD vector. An apparent full-length cDNA clone based on size (1.2 kbp), designated as pLHC2-cD-Neo, was isolated by colony hybridization and miniplasmid preparation analyses. To analyze for the expression of the Neo gene in human cells, the plasmid DNA was transfected into BEAS2B-R1 cells. Results indicated high level expression of the neo gene RNA as well as of the protein product in human bronchial epithelial cells based on the recovery of G418-resistent transfectants with efficiency indistinguishable from the control plasmid, pSV2-neo (FIG. 5).

Stable Episomal Maintenance of
EBO-pLHC2-cD-X Plasmids in Human Bronchial
Epithelial Cells and Utility of These Plasmids as Shuttle Vectors to Isolate Rare cDNA Clones To demonstrate that the EBO strategy of Margolskee et al. [Margolskee et al., Mol. Cell. Biol., 8:2837 (1988)] also functions in the pLHC2-cD vector system in human bronchial epithelial cells, the 7.5 kbp EBO segment was cloned at the Sfi1 site in pLHC2-cD-Neo. The resultant plasmid clone, designated as EBO-pLHC2-cD-Neo, was transfected into human epithelial cells. Human epithelial cell transformants were recovered which were resistant to both hygromycin B as well as G418 indicating the functional expression of both EBO and the neo genes in these cells (see legend of FIG. 5). The intact plasmid could be extracted not only in the Hirt supernatant from these transformants but also could be propagated back into bacteria, thereby demonstrating the shuttle nature of the EBO-pLHC2-cD vector which stably replicated episomally in multiple copies. It is evident from these data that the EBO strategy can be successfully exploited in the present modified vector system to facilitate the isolation of rare cDNA clones as well as in the parent Okayama-Berg vector system.

RNA:RNA Hybridization-Based Subtraction Method To Generate Subtracted RNA Probes Subsequent to the construction of pairs of cDNA libraries from a treated and control cell using methods well known in the art, the RNA:RNA subtraction can be performed as follows.

Radiolabeled (32P or 35S) and unlabeled RNAs from the two cDNA libraries to be subtracted (treated and control cell types, respectively) are synthesized in vitro. The radiolabeled RNAs are hybridized in solution with unlabeled, photobiotinylated RNAs in excess (Rot equivalent of over 1,000). The resulting photobiotinylated, double-stranded (ds) RNA:RNA hybrids, representing common sequences to be subtracted out between the two cell types, are removed from the hybridization mixture by streptavidin-agarose chromatography. The resultant radiolabeled, single-stranded (ss) RNAs, representing sequences expressed uniquely in treated cell type, can be used directly as probes for screening the cDNA library from treated cell type.

To exemplify the feasibility of this method and, moreover, to determine the efficiency of RNA:RNA hybridization-based subtraction, a simple mixing experiment was conducted with only two known species of RNAs: namely neo and 1.5 kb R1 RNAs synthesized in vitro from pLHC2-cD-Neo and pLHC2-cD-1.5 kb R1 (a randomly selected clone from BEAS2B-R1 cDNA library) plasmids, respectively, which were linearized with Notl digestion, in a T7 RNA polymerase-catalyzed reaction containing [32P]UTP, designated as T7/[32P]RNAs. The 1.5 kb R1/T7/[32P]RNAs were selectively subtracted out by hybridization with R1/SP6/unlabeled RNAs, since RNAs synthesized from Sall digested plasmid cDNA clones with SP6 RNA polymerase should be complementary to those synthesized with T7 RNA polymerase and, thus, should hybridize to form ds RNAs. From the ratios of 1.5 kb:Neo—specific RNAs before and after subtraction, efficiency of subtraction can be estimated as follows.

In Solution Hybridization: A 1:1 mixture of T7/[32P]RNA transcripts in tracer amounts corresponding to 1.5 kb and Neo cDNAs were hybridized in solution with 200-fold excess ("driver") of either unmodified or photobiotinylated SP6/Unlabeled 1.5 kb RNAs. The extent of in solution hybridization was determined by RNase A and T1 protection assay. Double-stranded (ds) RNAs are protected from the digestion whereas the single-stranded (ss) RNAs are completely digested to acid-soluble nucleotides by the RNases.

Subtraction by Hydroxylapatite (HAP) or Streptavidin-Agarose (SA) column chromatography: The ds [32P]/T7/1.5 kb: SP6/1.5 KB RNAs (unmodified or photobiotinylated) were subtracted out from ss [32P]/T7/Neo RNAs by binding to either HAP (for unmodified RNAs) or SA (for photobiotinylated) columns. In initial control experiments to work out the SA column chromatography, either unmodified or photobiotinylated [32P/T7/Neo RNA was used. As summarized in Table 1 (see below), less than 6% of the unmodified RNA bound to the column (presumably representing the non-specific binding) whereas almost 99% of the photobiotinylated RNAs could be bound to the column. In subsequent experiments, this non-specific binding was reduced to less than 2% by equilibrating the column with the binding buffer supplemented with 100 ug/ml of yeast tRNA as a carrier. Both HAP as well as SA column chromatographies worked equally well. However, when compared with SA, the HAP column chromatography is too cumbersome and time-consuming.

TABLE 1

BINDING OF UNMODIFIED OR PHOTOBIOTINYLATED [32p]/T7/NEO/RNA TO STREPTAVIDIN-AGAROSE:

| | UNMODIFIED RNA | | PHOTOBIO-TINYLATED RNA | |
|---|---|---|---|---|
| | TOTAL CPM 699,150 | PERCENT 100 | TOTAL CPM 574,000 | PERCENT 100 |
| 1ST WASH | 508,050 | 72.7 | 5,670 | 1.0 |
| 2ND WASH | 148,700 | 21.3 | 1,380 | 0.24 |
| 3RD WASH | 1,420 | 0.2 | 0 | 0 |
| UNBOUND | 658,170 | 94.14 | 7,050 | 1.23 |
| BOUND | 40,980 | 5.86 | 566,950 | 98.77 |

BINDING BUFFER: 10 mM TRIS, pH 7.2 - 0.1 M NaCl - 1 mM NaEDTA
SAMPLE: 1 UG RNA IN 0.1 ml BINDING BUFFER CONTAINING 100 UG OF YEAST tRNA AS CARRIER TO MINIMIZE NON-SPECIFIC BINDING TO STREPTAVIDIN-AGAROSE.

Dot blot hybridization analyses to quantitate the ratios of 1.5 kb:Neo-specific RNAs before and after subtraction: The [32P]/T7/1.5 kb- and Neo-specific RNAs were quantitated, before and after subtraction, by dot blot hybridization analyses as described herein. These data are summarized in Table 2 (see below). When only [32P]/T7/1.5 kb RNA was used as a probe (instead of 1:1 mixture of 1.5 kb:Neo RNAs), there was an estimated 12.4% cross-hybridization between 1.5 kb and Neo RNAs, presumably due to terminal 10–15 G and C residues in the complementary RNAs. Hence the data were corrected for the 12.4% background. With two cycles of in solution hybridization followed by SA chromatographic subtraction, about 97% of the 1.5 kb RNAs could be subtracted out from the original 1:1 mix of 1.5 kb: Neo RNAs.

TABLE 2

EFFICIENCY OF SUBSTRACTION OF UNHYBRIDIZED RNAs FOLLOWING RNA:RNA HYBRIDIZATION IN SOLUTION AS QUANTITATED BY BINDING TO EITHER STREPTAVIDIN-AGAROSE (PHOTOBIOTINYLATED RNA) OR TO HYDROXYLAPATITE (HAP, UNMODIFIED RNA) COLUMNS FOLLOWED BY DOT BLOT HYBRIDIZATION ANALYSES

| | SUBTRACTION METHOD: | | | | | |
|---|---|---|---|---|---|---|
| | STREPTAVIDIN-AGAROSE (TWO CYCLES) | | | HAP (ONLY ONE CYCLE) | | |
| NG 1.5KB AND NEO PLASMID DNA DOTTED | BEFORE | AFTER SUBTRACTION | PERCENT | BEFORE | AFTER SUBTRACTION | PERCENT |
| 1.5K/NEO MIXED RNA PROBE | RATIO OF 1.5KB:NEO RNA CPM BEFORE AND AFTER SUBTRACTION | | | | | |
| 50 | 1.29 | 0.087 | 93.3 | 1.68 | 0.28 | 83.4 |
| 10 | 1.26 | 0.028 | 97.8 | 1.95 | 0.24 | 87.6 |
| 5 | 0.95 | 0 | 100.0 | 1.14 | 0.22 | 80.6 |
| AVERAGE | | | 97.0 | | | 83.9 |
| 1.5KB RNA PROBE ALONE | RNA CPN BEFORE AND AFTER SUBTRACTION | | | | | |
| 50 | 2,104 | 72 | 96.6 | 4,083 | 259 | 93.7 |
| 10 | 463 | 17 | 96.3 | 944 | 107 | 88.7 |
| 5 | 173 | 0 | 100.0 | 370 | 36 | 90.3 |
| AVERAGE | | | 97.6 | | | 90.9 |

Efficiency of subtraction of unhybridized RNAs following RNA:RNA hybridization in solution as quantitated by binding to either streptavidin-agarose (photobiotinylated RNA) or to hydroxylapatite (HAP, unmodified RNA) columns followed by dot blot hybridization analyses.
RNAs were synthesized in vitro from appropriately restricted (NotI or SalI) pLHC2-cD-Neo or -1.5 kb R1 plasmid template DNAs in a T7 or SP6 RNA polymerase-catalyzed reaction. About 50 ng (tracer amounts) each of |32P|/T7/Neo and |32P|/T7/1.5 kb RNAs were hybridized in solution in a final volume of 10 ul with 10 ug (driver) of either unmodified or photobiotinylated SP6/1.5 kb RNA for 40 hrs at 50° C. (Rot equivalent of 443). The hybridization solution contained 40 mM PIPES, pH 6.4, 50% formamide, 3X SSPE, 0.1% SDS, and 20 ug/ml of poly(rA). The hybridization was carried out in a flame-sealed, 100 ul capillary. The extent of hybridization was quantitated by RNase A and T1 protection assay. Double-stranded (ds) RNAs are protected whereas single-stranded (ss) RNAs are degraded to acid-soluble nucleotides by digestion with the RNases. The resultant |32P|/T7/1.5 kb; unmodified or photobiotinylated SP6/1.5 kb ds RNAs were subtracted out from |32P|/T7/Neo ss RNAs by hydroxylapatite (HAP) or streptavidin-agarose (SA) column chromatography. HAP column chromatography was performed as follows: Briefly, hydroxylapatite (DNA Grade, BioRad Company) was packed in a water jacketed glass colum (BioRad Company, 1.0 × 2.0 cm). The column was equilibrated with 10 column volumes of Binding Buffer 0.14 M Na-PO4 buffer, pH 6.8, at 60° C. A sample containing ss and ds RNAs were loaded on the column in the Binding Buffer at 67° C. The column was washed with 5 column volumes of the buffer at the same temperature. Single- stranded RNAs were eluted off the column at 90° C. with the same buffer. Double-stranded RNAs were eluted with 0.3 M NaPO4, pH 6.8, at 90° C.
The ratios of 1.5 kb:Neo |32P|RNAs were quantitated before and after subtraction by dot blot hybridization analyses as follows:
Dot blot hybridization analyses: On a sheet of nylon membrane filter; 5, 10, and 50 ng quantities of pLHC2-cD-1.5 kb R1 and pLHC2-cD-Neo plasmid DNAs were dotted using a manifold filter device (Bethesda Research Laboratories, Inc.). Each of the dot contained 5 ug of salmon sperm DNA as a carrier. Following appropriate treatment of the filter, the hybridization was carried out at 65° C. for overnight using the |32P|RNAs, before and after subtraction, as probes. The hybridization solution contained 50% formamide, 3X SSPE, 0.1% SDS, 50 µg/ml of yeast RNA, and 10 ug/ml of poly(rA). Following post-hybridization washes of the filter, the dots were cut out to determine radioactivity by liquid scintillation. The data were corrected for about 12.4% cross-hybridization between 1.5 kb and Neo RNAs due to terminal C:C sequences as estimated from the hybridization data obtained when only 1.5 kb-specific |32P|RNAs were used as probe.

Phagemid-Derived cDNA Subtraction Library Construction Method

Phagemid-based subtraction cDNA library construction methods are currently available (Subtractor Kit of Invitrogen Company). The F1 DNA sequence in the phagemid vectors constitutes F1 filamentous phage replication origin that permits rescue of ss phagemid DNAs using an appropriate helper phage (R408) infection protocol and a suitable host bacterial strain (XL1Blue). However, these cloning vectors do not offer the advantages of vector-primed cDNA synthesis provided by the present pLHC2-cD vector system when the F1 sequence is cloned into the vector.

To adapt the phagemid-based subtraction protocol in the pLHC2-cD vector system, the F1 sequence was first cloned in the pLHC2-cD-Neo plasmid as shown in FIG. 6. A 582 bp NdeI/PvuII DNA fragment bearing F1 sequence from the phagemid, pBS(+) was recovered by agarose gel electrophoresis after conversion of NdeI restriction site to blunt-end by Klenow. The 582 bp F1 DNA fragment bearing blunt ends was ligated to synthetic ds SfiI linker DNA, digested with SfiI, gel purified, and then ligated to pLHC2-cD-Neo plasmid DNA which was previously digested with SfiI and CIP-treated.

Using the ss phagemid rescue method involving infection with helper phage R408, two recombinant clones with F1 sequence in opposite orientations of replication origin were picked. The recombinant bearing clockwise orientation of F1 replication origin was designated as pLHC2-cD-Neo-F1A and the other one, in opposite orientation, was designated as pLHC1-cD-Neo-F1B.

For conversion of ss to ds phagemid DNA, the AMV-RT, used in the Invitrogen Subtractor Kit, was compared with Klenow enzyme in terms of conversion efficiency of ss to ds phagemid DNA based on transformation efficiency of SCS-1 competent bacteria. As shown in Table 3 (see below), the transformation efficiency achieved with Klenow enzyme was about 270-fold higher than the one with AMV-RT when equivalent amount of ss phagemid DNA (1 ug) was used in the conversion process.

TABLE 3

The Relative Efficiencies of AMV RT and the Klenow Enzymes for Converting Single-Stranded (ss) to Double-Stranded (ds) PHagemid DNAs.

|  | YIELD (UG) | NUMBER OF COLONIES | (FOLD) |
| --- | --- | --- | --- |
| AMV-RT | 0.0826 UG | $2.0 \times 10^4$/UG | (1) |
| KLENOW | 0.675 UG | $5.4 \times 10^6$/UG | (270) |

The reaction mixture for AMV-RT contained 50 mM Tris-HCl, pH 8.5 - 8 mM MgCl - 30 mM KCl - 0.3 mM DTT - 2 mM dNTPs - 30 ng SP6 primer - 1 ug ss circular phagemid DNA template - 40 U AMV-RT - 10 uCi [32P]dCTP in a total volume of 40 ul and was incubated at 42° C. for 60 min. The reaction mixture for Klenow enzyme contained 100 mM HEPES, pH 6.9 - 10 mM MgCl - 2.5 mM DTT - 70 mM KCl - 2 mM dNTPs - 30 ng SP6 primer - lug as circular phagemid DNA template - 25 U Klenow enzyme - 10 uCi[32P]dCTP in a total volume of 40 ul and was incubated at 15° C. for 4 hrs. The amount of ss to ds phagemid DNA conversion (yield) was calculated based on TCA-precipitated radio-labeled nucleic acids. The transformation efficiency was determined using competent SCS-1 bacteria which produced $6.0 \times 10^8$ colonies per ug supercoiled pBR322.

The F1 DNA sequence (582 bp with Sfi1 cohesive ends) was then cloned into the pLHC2-CG5, the source plasmid for the preparation of dC-tailed linker DNA in vector-primed cDNA synthesis protocol, at the unique Sfi1 restriction site. The resultant clone was designated as pLHC2-CG6 (shown in FIG. 7). Double-stranded cDNA library now constructed (from TGF-beta1-treated (4 hrs) human bronchial epithelial cell line, BEAS2B-S6, poly(A)+ RNA preparation) in the phagemid vector system pLHC2-cD-F1A (utilizing dT-tailed vector-primer prepared from pLHC2-HO2 and dC-tailed linker DNA of about 1.2 kb prepared from pLHC2-CG6) can be converted to a ss phagemid DNA using the F1A origin of DNA replication. As shown schematically in FIG. 8, SP6 promoter-driven ss RNAs are synthesized in vitro from a "control" cDNA library plasmid DNA linearized with SalI or SacI digestion, photobiotinylated, and then hybridized in solution with excess (Rot equivalent of over 1,000) of ss phagemid DNAs derived from a "treated" cDNA library (DNA:RNA hybridization). The common sequences between the "control" and "treated" cell type cDNA libraries should hybridize to form ds DNA:RNA-photobiotin hybrid which can be removed, and hence subtracted out, by SA chromatography. The resultant subtracted phagemid DNAs in ss form can be enzymatically converted to ds form by the Klenow fragment of DNA polymerase I. The ds DNAs, subsequently, be used to transform appropriate host competent bacteria by electroporation. This ultimately constitutes a SUBTRACTED cDNA LIBRARY. Once the subtraction is accomplished, the F1A DNA sequence in the expression cDNA library constructed in the phagemid vector system is no longer required and hence can be simply substituted with the 7.5 kbp EBO DNA segment at the Sfi1 restriction site. The EBO-SUBTRACTED cDNA LIBRARY can then transfected into mammalian cells to screen for specific cDNA clones based on a given phenotype according to the EBO strategy of Margolskee et al. (1988) as described above.

In Vivo Synthesis of Antisense RNA Approach to Enrich cDNA Libraries

As described above, antisense RNAs can be synthesized in vitro off the SP6 promoter from cDNA inserts within the phagemid vector system by SP6 RNA polymerase (SP6RNP). Additionally, if the SP6RNP gene can be expressed as a biologically active enzyme product and can be efficiently translocated into nuclei of mammalian cells, the present vector system also offers the potential of trans-activating the SP6 promoter-driven over-expression of anti-sense RNAs off the cDNA inserts in vivo in mammalian cells. Low level expression in vivo of the procaryotic SP6RNP gene under an eucaryotic transcriptional control would probably be sufficient to transactivate the SP6 promoter-driven over-expression of antisense RNAs because of the enzymatic amplification involved. The over-expression of antisense RNAs can be expected to inhibit the translation of sense RNAs which would be expressed from the cDNA inserts under the control of SV40 transcriptional elements in the EBO-pLHC2-cD vector when cotransfected. Since the transactivation process must take place in the nucleus of eucaryotic cells, it is prerequisite that SP6RNP enzyme protein, which would be expressed from co- or pre-transfected SP6RNP gene construct preferably under the control of an inducible eucaryotic promoter, such as metallothionine or heat shock promoters, be physically translocated in the nucleus in its functional form. Since the protein is of about 100 kd size and of procaryotic origin, it is unlikely that it would be translocated into the nucleus by simple diffusion without the aid of a required nuclear targeting sequence.

With the in vivo synthesis of antisense RNA approach of the present invention, the present phagemid subtraction cDNA vector system can further potentiate the EBO strategy (described above) in enriching subtraction cDNA libraries based on a given phenotype in mammalian cells. This approach can particularly be fruitful in identifying genes involved in the regulation of growth inhibition, terminal differentiation, tumor suppression, senescence, etc. where conventional approaches are unproductive. The following case, being particularly pursued in the inventors' laboratory, exemplifies the strategy.

The S6 and R1 clones of the parent BEAS2B cell line, which is SV40 T-antigen mediated immortalized, but non-tumorigenic, human bronchial epithelial cell line, represent sensitive and resistent cell lines, respectively, to undergo transforming growth factor beta 1 (TGF-beta 1)-induced squamous terminal differentiation [Ke et al., Differentiation, 38:60 (1988)]. A differentiation-specific subtraction cDNA library is constructed in the EBO-pLHC2-cD vector system of the present invention, as described above, by subtracting out R1 cell-specific common cDNA sequences. When this differentiation-specific library DNA is co- or pre-transfected with the SP6RNP gene construct into growth-inhibited S6 cells previously treated with TGF-beta 1, the over-expression of antisense RNAs should abolish the growth inhibition as a result of turning off the translation of sense RNAs expressed specifically from growth-controlling genes. Consequently, the only hygromycin B-resistent transformants of S6 cell colonies that survive and propagate in growth medium supplemented with TFG-beta 1, would be the ones which should be highly enriched in differentiation-specific expressed genes involved in the growth inhibition control.

All publications mentioned hereinabove are hereby incorporated by reference.

The foregoing invention has been described in some detail for purposes of clarity and understanding. It will also be obvious that various combinations in form and detail can be made without departing from the scope of the invention.

What is claimed is:

1. A method of constructing a subtracted cDNA library for use in phenotypic selection of genes, comprising the steps of:

a) constructing a first cDNA library from a first population of cells;

b) cloning a cDNA fragment from said first cDNA library into an eukaryotic expression vector characterized by having functional properties of in vitro and in vivo synthesis of sense RNA and of in vitro and in vivo synthesis of antisense RNA for cDNA subtraction based on DNA:RNA hybridization and in vivo synthesis of antisense RNA for phenotypic selection of genes, said eukaryotic expression vector having functional properties corresponding to those exhibited by an expression vector generated from a first source plasmid PLHC2-HO2 (FIG. 1) and a second source plasmid PLHC2-CG6 (FIG. 7);

c) constructing a second cDNA library from a second population of cells from the same organism as said first population of cells but having a differential gene expression relative to said first population of cells;

d) cloning a cDNA fragment from said second cDNA library into said eukaryotic expression vector of step (b);

e) generating single-stranded DNA from said first cDNA library by use of a phage replication origin in said eukaryotic expression vector of step (b);

f) treating the second cDNA library with a polymerase specific to a bacteriophage polymerase promoter of said eukaryotic expression vector of step (b), said bacteria phage polymerase promoter being in the opposite orientation as that of said phage replication origin to generate a group of RNA molecules;

g) forming DNA:RNA hybrids of said single-stranded DNA and said group of RNA molecules;

h) separating said DNA:RNA hybrids of step (g) from unhybridized single stranded DNA, thereby isolating a subtracted group of single-stranded DNA; and i) converting the isolated single-stranded cDNA to double stranded DNA by use of a DNA polymerase to form a subtracted library; and j) using said subtracted library for phenotypic selection of genes.

2. The method of claim 1, wherein said eukaryotic vector further comprises:

a sequence providing for episomal replication in eukaryotic cells, wherein a cDNA cloned into said eukaryotic expression vector including the sequence for episomal replication, is oriented as shown in FIG. 3 or an equivalent vector of said eukaryotic expression vector including the sequence for episomal replication, which retains the functional properties and features of said eukaryotic expression vector including the sequence for episomal replication; wherein said functional features retained include episomal replication and in vivo synthesis of antisense RNA for phenotypic selection of genes.

* * * * *